United States Patent [19]

Duffett

[11] Patent Number: Plant 6,885

[45] Date of Patent: Jun. 27, 1989

[54] CHRYSANTHEMUM PLANT NAMED FLEX

[75] Inventor: William E. Duffett, Salinas, Calif.

[73] Assignee: Yoder Brothers, Barberton, Ohio

[21] Appl. No.: 170,452

[22] Filed: Mar. 18, 1988

[51] Int. Cl.[4] ..... A01H 5/00
[52] U.S. Cl. ..... Plt./78
[58] Field of Search ..... Plt./78

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Flex particularly characterized by its flat capitulum form; decorative capitulum type; yellow ray floret color; diameter across face of capitulum of up to 9 cm at maturity; uniform nine week photoperiodic flowering response to short days; peduncle length ranging from 17 to 22 cm on open, terminal sprays; and tall plant height when grown as a single stem spray cut mum.

3 Drawing Sheets

The present invention comprises a new and distinct cultivar of Chrysanthemum, botanically known as *Dendranthema grandiflora,* and referred to by the cultivar name Flex.

Flex, identified as 79D82002, was originated from a cross made by William E. Duffett in a controlled breeding program in Salinas, Calif. in 1979.

The female parent and the male parent of Flex were both unnamed seedlings, identified respectively as 73348096 and 78121001.

Flex was discovered and selected as one flowering plant within the progeny of the stated cross by William E. Duffett in December 1979 in a controlled environment in Salinas, Calif.

The first act of asexual reproduction of Flex was accomplished when vegetative cuttings were taken from the initial selection in March 1980 in a controlled environment in Salinas, Calif., by technicians working under formulations established and supervised by William E. Duffett.

Horticultural examination of controlled flowerings of successive plantings has shown that the unique combination of characteristics as herein disclosed for Flex are firmly fixed and are retained through successive generations of asexual reproduction.

Flex has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Flex, which, in combination, distinguish this Chrysanthemum as a new and distinct cultivar:

1. Flat capitulum form.
2. Decorative capitulum type.
3. Yellow ray floret color.
4. Diameter across face of capitulum up to 9 cm at maturity.
5. Uniform nine week photoperiodic flowering response to short days.
6. Peduncle length ranging from 17 to 22 cm on open terminal sprays.

7. Tall plant height, requiring one long day week prior to short days to attain a flowered plant height of 90 to 100 cm for year-round flowerings.

The accompanying photographic drawings show typical inflorescence and leaf characteristics of Flex, with the colors being as nearly true as possible with illustrations of this type.

Sheet 1 is a color photograph of Flex grown as a single stem cut spray mum.

Sheet 2 is a black and white photograph of three views of the inflorescence of Flex.

Sheet 3 is a black and white photograph showing the upper and under sides of the leaves of Flex at three stages of development (mature, intermediate and immature).

Of the commercial cultivars known to the inventor, the most similar in comparison to Flex is Golden Polaris. Reference is made to Chart A, which compares certain characteristics of Flex to the same characteristics of Golden Polaris.

Similar traits are ray floret color, capitulum form and type, plant height and flowering response. The peduncle length of Flex is slightly longer and the diameter of capitulum is larger than Golden Polaris.

In the following description, color references are made to the Royal Horticultural Society Colour Chart. The color values were determined on plant material grown in Salinas, Calif. on Oct. 14, 1976.

Classification:

*Botanical.*—*Dendranthema grandiflora,* cv Flex.
*Commercial.*—Decorative cut spray mum.

INFLORESCENCE

A. Capitulum:
*Form.*—Flat.
*Type.*—Decorative.
*Diameter across face.*—Up to 9 cm at maturity.

B. Corolla of ray florets:
*Color (general tonality from a distance of three meters).*—Yellow.
*Color (upper surface).*—6A.
*Color (under surface).*—7D.
*Shape.*—Flat, oblong.

C. Corolla of disc florets:
*Color (mature).*—Closest to 5A.
*Color (immature).*—Closest to 150B.

D. Reproductive organs:

*Androecium.*—Present on disc florets only; very few disc florets, covered by ray florets.

i Gynoecium.—Present on both ray and disc florets.

PLANT

A. General Appearance:

*Height.*—Tall; 90 to 100 cm as a single stem cut mum with one long day week prior to short days.

B. Foliage:

*Color (upper surface).*—147A.

*Color (under surface).*—147B.

*Shape.*—Lobed and slightly serrated.

CHART A

COMPARISON OF FLEX AND GOLDEN POLARIS

| | Flex | Golden Polaris |
|---|---|---|
| Ray floret color | Yellow | Yellow |
| Capitulum form and type | Flat Decorative | Flat Decorative |
| Spray formation | Terminal 17 to 22 cm peduncles | Terminal 15 to 20 cm peduncles |
| Diameter across face of capitulum | Up to 9 cm | Up to 8 cm |
| Plant height | Tall | Tall |
| Flowering response period | 9 weeks | 9 weeks |

COMPARISONS MADE OF PLANTS GROWN AS SINGLE STEM SPRAY CUT MUMS IN SALINAS, CALIFORNIA

I claim:

1. A new and distinct Chrysanthemum plant named Flex, as described and illustrated, and parts thereof.

* * * * *

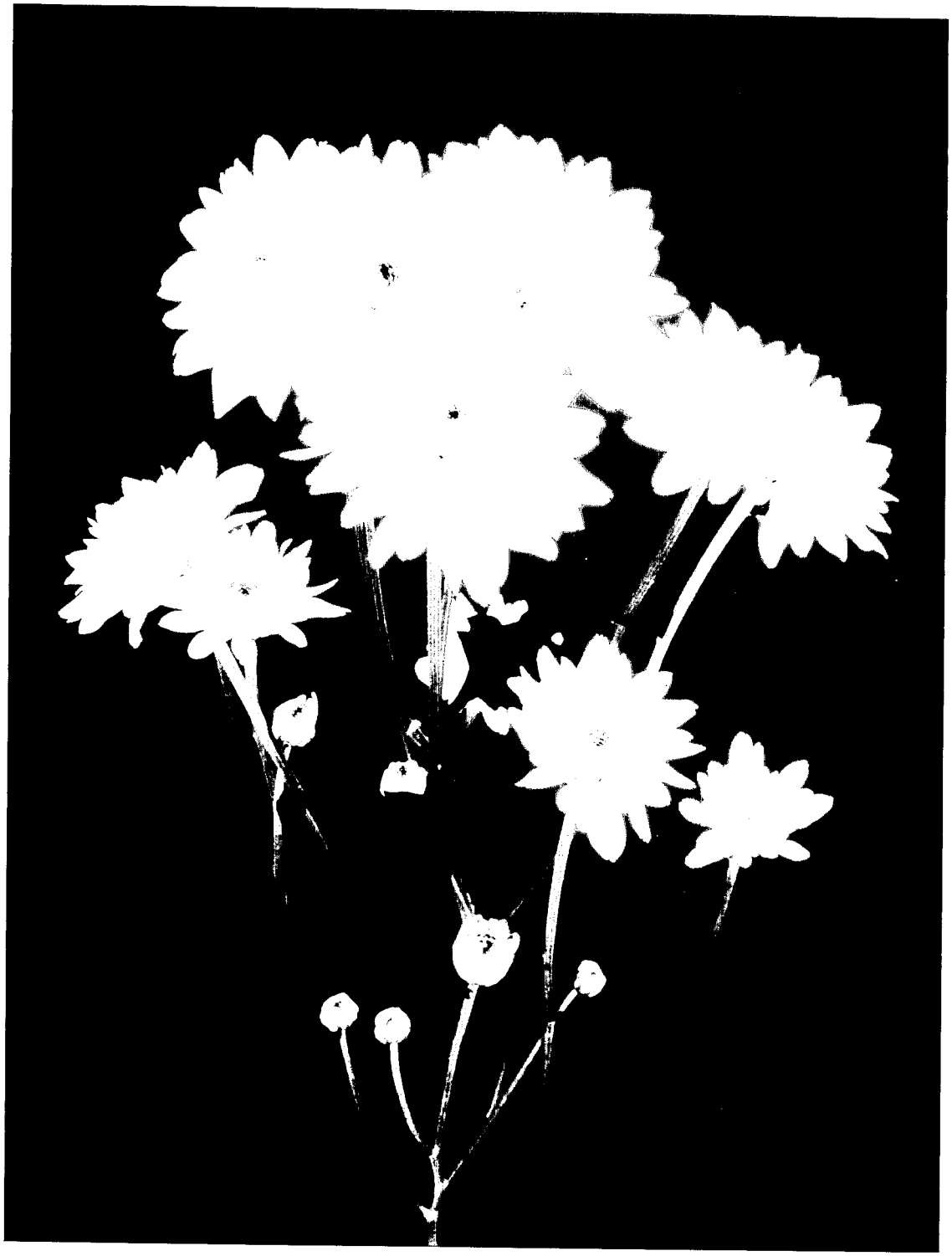

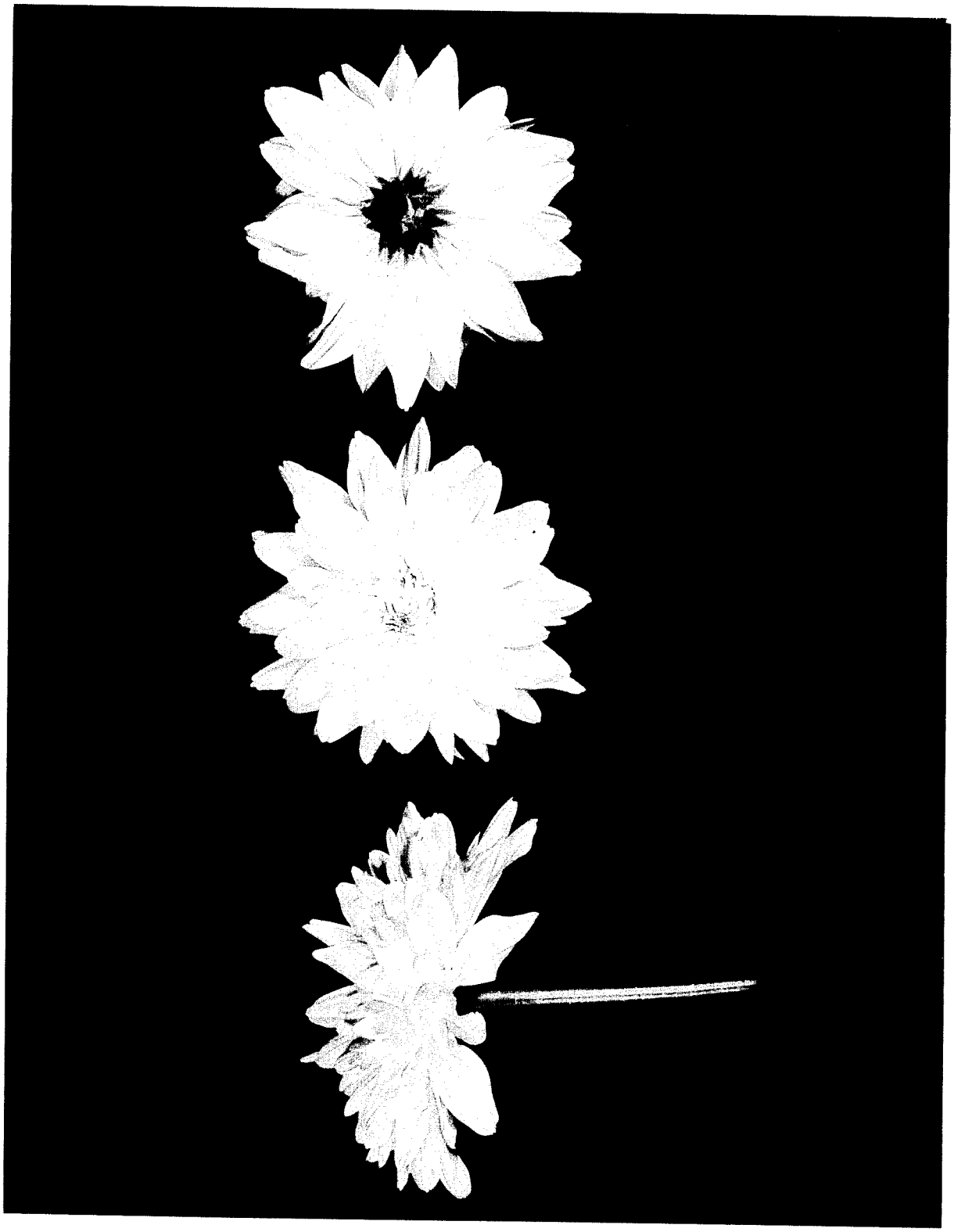

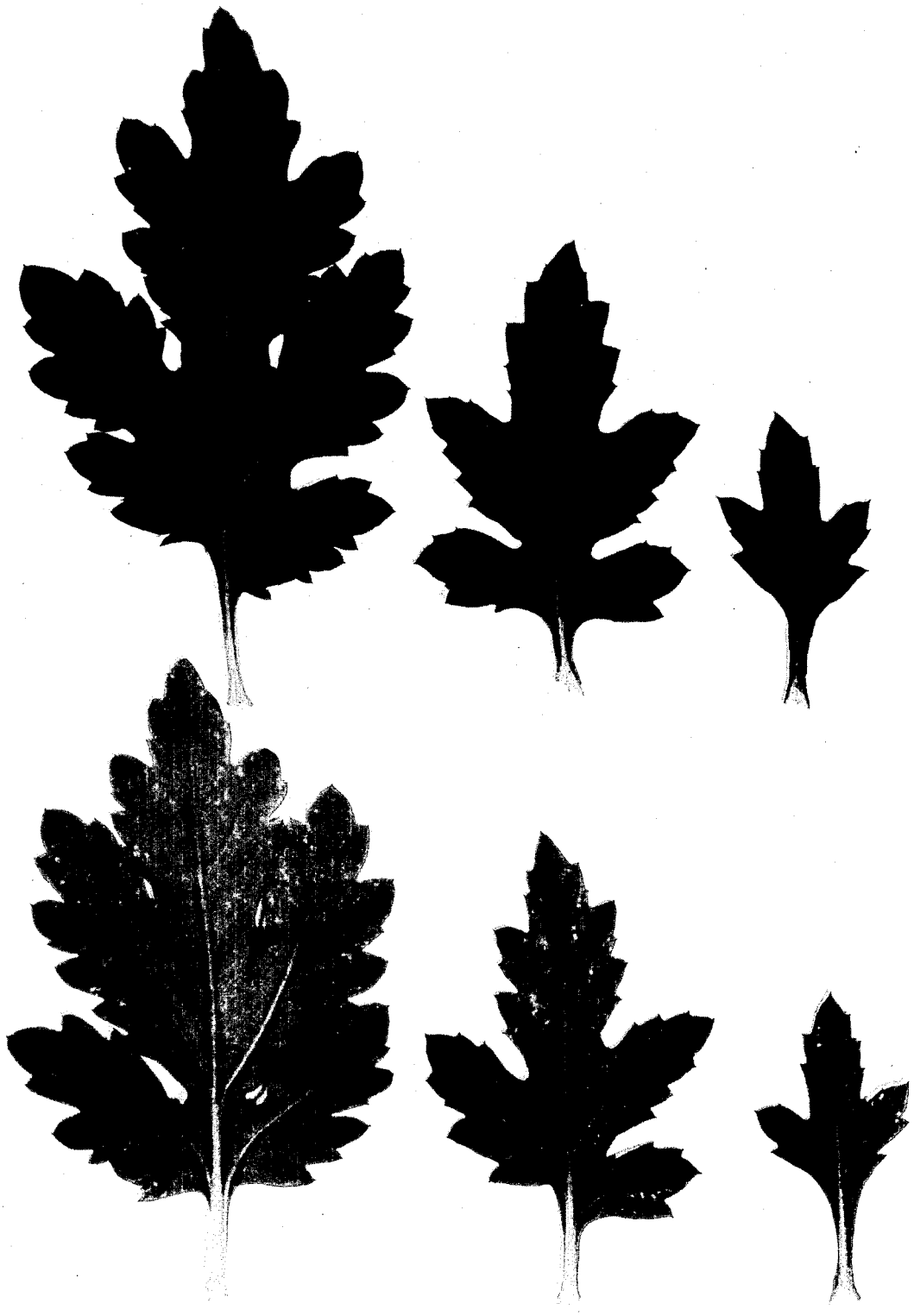

UNITED STATES PATENT AND TRADEMARK OFFICE

CERTIFICATE OF CORRECTION

PATENT NO. : PP 6,885

DATED : June 27, 1989

INVENTOR(S) : William E. Duffett

It is certified that error appears in the above—identified patent and that said Letters Patent is hereby corrected as shown below:

Column 2, Line 28, "1976" should be "1987"

Column 3, Line 4, before "Gynoecium" the "i" should not appear.

Signed and Sealed this

Twenty-sixth Day of June, 1990

*Attest:*

HARRY F. MANBECK, JR.

*Attesting Officer*

*Commissioner of Patents and Trademarks*